United States Patent [19]

Sifniades et al.

[11] 4,062,839

[45] Dec. 13, 1977

[54] RESOLUTION OF α-AMINO-ε-CAPROLACTAM OPTICAL ISOMERS

[75] Inventors: Stylianos Sifniades, Madison; William J. Boyle, Jr., Warren, both of N.J.

[73] Assignee: Allied Chemical Corporation, Morris Township, N.J.

[21] Appl. No.: 723,830

[22] Filed: Sept. 16, 1976

[51] Int. Cl.² .......................................... C07D 223/10
[52] U.S. Cl. ............................................. 260/239.3 R
[58] Field of Search ................................ 260/239.3 R

[56] References Cited

U.S. PATENT DOCUMENTS

| 3,692,775 | 9/1972 | Kubanek et al. | 260/239.3 R |
| 3,824,231 | 7/1974 | Kubanek et al. | 260/239.3 R |

*Primary Examiner*—Henry R. Jiles
*Assistant Examiner*—Robert T. Bond
*Attorney, Agent, or Firm*—Robert A. Harman; Ernest A. Polin

[57] ABSTRACT

A complex containing three moles of alpha-amino-e-caprolactam and one mol of magnesium chloride, as such or containing also one mol of ethanol or isopropanol. The complex is useful for resolution of the alpha-amino-e-caprolactam optical isomers, in supersaturated solution containing ethanol, isopropanol, or methanol by contacting such solution with crystals of the complex.

5 Claims, No Drawings

RESOLUTION OF α-AMINO-E-CAPROLACTAM OPTICAL ISOMERS

BACKGROUND OF THE INVENTION

The resolution is broadly known of alpha-amino-e-caprolactam (hereinafter "ACL") optical isomers (hereinafter D-ACL, L-ACL, and D,L-ACL for the dextro- and levorotary isomers and the racemic mixture respectively), by crystallization of certain ACL compounds on seed crystals, from solution. Illustrative is U.S. Pat. No. 3,824,231 of July 16, 1974 to Kubanek et al. entitled "Resolution of α-Aminocaprolactam." This patent discloses complexes of ACL with nickel, cobalt, copper, iron and zinc and use of the L-complex or the D-complex to resolve D, L-ACL mixtures from solution in solvents such as methanol, ethanol and isopropanol. The patent also discloses that in practical operations, the solution to be resolved is passed over alternating beds of L- and D-seed crystals. Thereby, the solution is separated in a number of resolution stages into purified L-ACL and D-ACL. If, as commonly would be the case, the L-ACL is the desired product then the D-ACL is submitted to racemization to convert it to D,L-ACL which is then submitted to further resolution by the subject process.

SUMMARY OF THE INVENTION

In the present invention, the magnesium chloride complex of ACL is obtained and is used for resolution of D,L-ACL in the same general manner as are the complexes disclosed in the above noted U.S. Pat. No. 3,824,231. The magnesium chloride complex has advantage in being a low cost, nontoxic material. It should be recognized that not all salts, even those which are soluble in alcohols, will function to form complexes with ACL; and even if complexes are formed, these will not in general function for purposes of resolving the optical isomers of ACL. Moreover, the complexes of ACL disclosed in U.S. Pat. No. 3,824,231 all contain transition metal ions whereas magnesium chloride is a salt of an alkaline earth metal. So far as we are aware, no alkaline earth metal salt complex with ACL, except complexes containing magnesium chloride, can be resolved by the above noted crystallization procedures. In particular, our tests indicate no resolution in the precipitate obtained upon crystallization of a complex of ACL and calcium chloride from isopropanol. Hence, the utility of this magnesium chloride complex for this resolution would not have been obvious.

The complex of this invention contains 3 mols of ACL and 1 mol of magnesium chloride and can contain also, when in crystalline form, 1 mol of ethanol or isopropanol. The general method of employing the complex for resolution of D,L-ACL optical isomers is to form a supersaturated solution of the isomer mixture and magnesium chloride in a solvent containing ethanol, isopropanol or methanol or a mixture thereof; then to contact the solution with seed crystals of the ACL-/magnesium chloride complex. When one or the other isomer is the desired product, the solution must of course contain adequate concentration of that isomer; and complex predominating in that isomer is used as the added seed crystals. The complex of exclusively the same isomer as that predominating in the seed crystals, we have found, crystallizes out from a supersaturated solution having above or even somewhat below the racemic composition in that isomer, on such seed crystals, very much preferentially to complexes containing the other isomer. The resulting crop of crystals can then be recovered and further processed by the methods described in the above noted U.S. Pat. No. 3,824,231. Usually, as in that patent disclosure, the complex of the L-ACL isomer is the desired product which is recovered.

DESCRIPTION OF THE PREFERRED EMBODIMENTS

The general operation of our process will be understood from the foregoing. Preferably in preparing the solution, the ACL complex to be resolved and magnesium chloride are admixed at about 3:1 mol ratio in the solvent. Temperatures for such operation can be as indicated in U.S. Pat. No. 3,824,231; i.e. from about 10° C. up to about 100° C. The preferred solvents consist essentially of ethanol or isopropanol.

For use as seeds in resolving the optical isomers, it is desirable to employ small crystals of the complex. These can be formed by known means, for example by adding to a solution of the complex a large proportion of a poor solvent for the complex, for example diethyl ether. Preferably for preparing seed crystals, a relatively pure isomer of ACL will be used such that the seed crystals have optical purity of at least about 90%.

The preferred temperature for the resolution which occurs, upon contacting the solution of ACL complex with crystals of the complex of the desired optical isomer, will be about 15° C. to about 80° C; in particular about room temperature.

The examples which follow are illustrative of our invention and of the best mode which we have contemplated for carrying out the invention but are not to be interpreted in a limiting sense.

In Examples 1–3 illustrating production of L-ACL/magnesium chloride complexes (Exs. 1, 2) and D,L-complex (Ex. 3), a solution of ACL isomer was mixed in mol ratio of about 3:1 with a solution in the same solvent of anhydrous magnesium chloride, added thereto while stirring with a magnetic stirrer at about 40° C., using the solvents indicated in Table 1 below. The resulting white crystals were filtered, washed as indicated, and dried in vacuo as indicated. Results are shown in the Table, where "E.W./Cl" is equivalent weight per gram-equivalent of chloride ion in the product, and "E.W./base" is equivalent weight per gram-equivalent of base (i.e. ACL) in the product, and "M.P." is melting point of the product.

In Examples 4 and 5, use of the complex for resolution of D,L-ACL is illustrated. A quantity of (D,L-ACL)$_3$.MgCl$_2$.EtOH complex was dissolved in ethanol. Then crystals of (L-ACL)$_3$.MgCl$_2$.EtOH complex were added and the mixture was stirred periodically at room temperature by a magnetic bar stirrer, in a sealed glass vessel, for 10 seconds at 10 minute intervals. The solids obtained were filtered, washed with ethanol, and vacuum dried. The data are shown in Table 2.

Table 1

Preparation of Complex

| Ex. | Starting ACL Isomer; (Optical Purity); Weight | Solvent | Wash Liquid | Drying | M.P. °C. | Yield (% Th'l) | Rot'n $[d]_D^{25}$, pure | Rot'n of Product | E.W./Cl; (Theory) | E.W./base: (Theory) |
|---|---|---|---|---|---|---|---|---|---|---|
| 1 | L-(94.6%) 4.00 g | EtOH 19 ml. | EtOH | 60° C. 1 hr. | — | 68% | −24.9 (c=5, 1N HCl) | −24.9 | 272 (263) | — (175) |
|   |   |   |   | 115° C. 1 hr. add'l | 262–4° |   |   | −26.2 (indicating loss of EtOH) | 252 | 176 |
| 2 | 5.34 g | i-PrOH ca. 10 ml. | i-PrOH | 115° C. 1 hr. | 263–4° | ca. 20%* | −24.2 | −24.6 | 270 (270) | 179 (180) |
| 3 | D,L- 4.00 g | EtOH;(17 ml.) then 10 vols. Et$_2$O added | Et$_2$O | 115° C. 1 hr. | 250–75° | 78% | 0 | — | 255 (263) | 173 (175) |

*The crystals were obtained upon adding 64 mg of L-(ACL)$_3$MgCl$_2$ complex as seed; they were extremely small and hence difficult to filter and wash. The weight after drying was 659 mg.

Table 2

Resolution of D,L-ACL Complex

| Ex. | Wgt. of Starting Complex; conc. (w/w) | Seed Crystal; Rotation $[d]_D^{25}$ | Crystallizing Time in min. | Drying Temp. | Wgt. of Seeds | Wgt. of Product | Rotation of Product | M.P. of Product | Ratios in % (a) | (b) | (c) |
|---|---|---|---|---|---|---|---|---|---|---|---|
| 4 | 0.4995g 25% | −24.9 | 205 | 100°–120° | 0.1141g | 0.1448g | −23.77 | 254–5° C. (with release of gases) | 95.5 | 21.1 | 9.6 |
| 5 | 0.799 36% | −24.9 | 90 | 75° C. | 0.105g | 0.160g | −24.2 | — | 97 | 47.5 | 12.5 |

(a) = αProd: αSeed;
(b) = Wgt. of L-complex seeded out: wgt. L-complex as seed;
(c) = Wgt. of L-complex seeded out: Wgt. of L-complex in original soln.

EXAMPLE 6

This example illustrates operativeness of methanol as a solvent for resolution of D,L-ACL by use of the complex formed with magnesium chloride.

0.704 g. of ACL of 68% optical purity in L-isomer was made up from 0.530 g. (3 parts) of L-ACL of 90.3% optical purity and 0.174 g. (1 part) of D,L-ACL, amounting to 5.50 mmols. To this was added with stirring, 2.50 ml. of a 1.096N solution of MgCl$_2$ in methanol, amounting to 2.74 mmols, and about 5 ml of diethyl ether. Two liquid layers formed.

Stirring was continued for three days, during which time white crystals formed. The crystals were filtered off, washed with 2:1 (by vol) of ether/methanol, and dried in vacuo at 40° C. This product sintered at 275° C., became yellow, and melted and foamed at 300° C.

The equivalent weight of this product per gram-equivalent of chloride ion contained therein was 245 g. (theory for (ACL)$_3$.MgCl$_2$=240). Optical rotation: $[\alpha]_D$ = −22.2 (C=5, 1N HCl; pure= −26.6). The optical purity (αprod.:αpure)=83.3%.

The improvement in optical purity over the starting value of 68%, obtained by crystallizing the mixed isomers from methanol, indicates that the predominant isomer in the original mixture (the L-complex) crystallized out preferentially on the L-complex crystals formed. It will be noted from the equivalent weight data that little or no alcohol was contained in the (ACL)$_3$.MgCl$_2$ complex formed in this example.

We claim:

1. A complex containing three mols of alpha-amino-e-caprolactam and one mol of magnesium chloride.

2. Crystalline complex of claim 1, containing one mol of ethanol or isopropanol.

3. Process of obtaining at least partial separation of a mixture of D- and L-isomers of alpha-amino-e-caprolactam, comprising forming a supersaturated solution of such mixture and magnesium chloride, in a solvent containing ethanol, isopropanol or methanol or a mixture thereof; then contacting the solution with seed crystals of complex as defined in claim 1, predominantly containing the desired isomer of aminocaprolactam.

4. Process of claim 3 wherein the solvent consists essentially of ethanol or isopropanol; the solution contains a mol ratio of aminocaprolactam:magnesium chloride of about 3:1; the solution initially has at least about the racemic composition in the desired isomer; and the seed crystals are at least about 90% optically pure in the desired isomer, whereby that same isomer crystallizes from the solution preferentially to the other isomer.

5. Process of claim 4 wherein the solvent is ethanol; the complex used as seed crystals corresponds essentially to the formula (ACL)$_3$.MgCl$_2$.EtOH where ACL represents one or the other optical isomer of alpha-amino-e-caprolactam; the temperature is in the range of 15° C.–80° C.; and the crystallized complex of (ACL)$_3$.MgCL$_2$.EtOH is recovered as product.

* * * * *